United States Patent [19]

Magnante

[11] Patent Number: 4,702,576
[45] Date of Patent: Oct. 27, 1987

[54] OCULAR SCATTERING ANALYZER

[75] Inventor: Peter C. Magnante, West Brookfield, Mass.

[73] Assignee: Cambridge Instruments Inc., Buffalo, N.Y.

[21] Appl. No.: 780,477

[22] Filed: Sep. 27, 1985

[51] Int. Cl.$^4$ .......................... A61B 3/10; A61B 13/00
[52] U.S. Cl. .................................... 351/214; 351/221; 128/745
[58] Field of Search ............... 351/205, 206, 214, 221; 128/633, 745

[56] References Cited

U.S. PATENT DOCUMENTS

4,350,163  9/1982  Ford, Jr. ......................... 351/246 X

Primary Examiner—Rodney B. Bovernick
Attorney, Agent, or Firm—Alan H. Spencer

[57] ABSTRACT

A method and apparatus for non-invasive in vivo inspection of ocular tissue wherein a laser provides a low power, coherent and uniform output beam of light which is guided through the optical system of a modified slit lamp biomicroscope to the eye of a patient for scattering by protein molecules in the ocular tissue of the patient, and scattered laser light in the ocular tissue is viewed through the slit lamp to visually align a pick up associated with the slit lamp optical system to a desired location in the ocular tissue. A measurement is performed by receiving laser light scattered from the ocular tissue and converting the scattered light into an electrical signal, and the electrical signal is analyzed by sorting it into components each characterized by an intensity and a fluctuation rate and each component associated with a protein group in the ocular tissue.

20 Claims, 14 Drawing Figures

OCULAR SCATTERING ANALYZER

BACKGROUND OF THE INVENTION

This invention relates to the art of light scattering spectroscopy, and more particularly to a new and improved method and apparatus for inspection of ocular tissue.

One area of use of the present invention is facilitating the early detection of cataracts and other anterior segment eye diseases, although the principles of the present invention can be variously applied. Quasi-elastic light scattering is a useful method to determine the size distribution of sub-micron particles in fluids. Slit lamp biomicroscopy is a proven, accepted and effective method widely employed in ophthalmic diagnosis. In accordance with this invention it would be highly desirable to utilize these methods for non-invasive in vivo inspection of ocular tissue.

SUMMARY OF THE INVENTION

It is, therefore, a primary object of this invention to provide a new and improved method and apparatus for inspection of ocular tissue.

It is a further object of this invention to provide such a method and apparatus which can be employed in a non-invasive, in vivo manner.

It is a further object of this invention to provide such a method and apparatus which utilizes a combination of quasi-elastic light scattering and slit lamp biomicroscopy.

It is a further object of this invention to provide such a method and apparatus which is efficient, effective, reliable and economical.

The present invention provides a method and apparatus for non-invasive in vivo inspection for ocular tissue wherein a laser provides a low power, coherent and uniform output beam of light which is guided through the optical system of a modified slit lamp biomicroscope to the eye of a patient for scattering by protein molecules in the ocular tissue of the patient, and scattered laser light in the ocular tissue is viewed through the slit lamp to visually align a pick up associated with the slit lamp optical system to a desired location in the ocular tissue. A measurement is performed by receiving laser light scattered from the ocular tissue and converting the scattered light into an electrical signal, and the electrical signal is analyzed by sorting it into components each characterized by an intensity and a fluctuation rate and each component associated with a protein group in the ocular tissue. In particular, the electrical signal is analyzed by measuring time dependent fluctuations of the signal and calculating the autocorrelation function associated with the fluctuations, matching the autocorrelation function with a two-component exponential decay curve, computing the amplitudes and fluctuation rates of the two components, and utilizing the amplitudes and fluctuation rates of the two components by relating them to two species of protein in the ocular tissue whereby the relative degree of laser light scattering by the two protein species provides information as to the condition of the ocular tissue. The slit lamp is modified by providing means for introducing the laser output light beam to the illumination optical system of the slit lamp in a manner such that the laser light beam is guided to the patient's eye along the same direction as slit of light from the lamp, and by providing means operatively associated with the viewing optical system of the slit lamp for receiving scattered laser light from the patient's eye, the receiving means including means defining a visible target for aligning the laser light visually with the slit of light relative to the patient's eye.

The foregoing and additional advantages and characterizing features of the present invention will become clearly apparent upon a reading of the ensuing detailed description together with the included drawing wherein:

DETAILED DESCRIPTION OF THE ILLUSTRATED EMBODIMENTS

Protein in the tissue of the eye undergoes random diffusive movement due to continuous bombardment of neighboring molecules. When a coherent, steady beam of light is scattered by the moving proteins, the scattered light is no longer steady but fluctuates in time. The rate of fluctuation of the scattered light is determined by the movement of the protein. Small proteins generally will move faster than large proteins in the same cellular environment.

Figure 1:
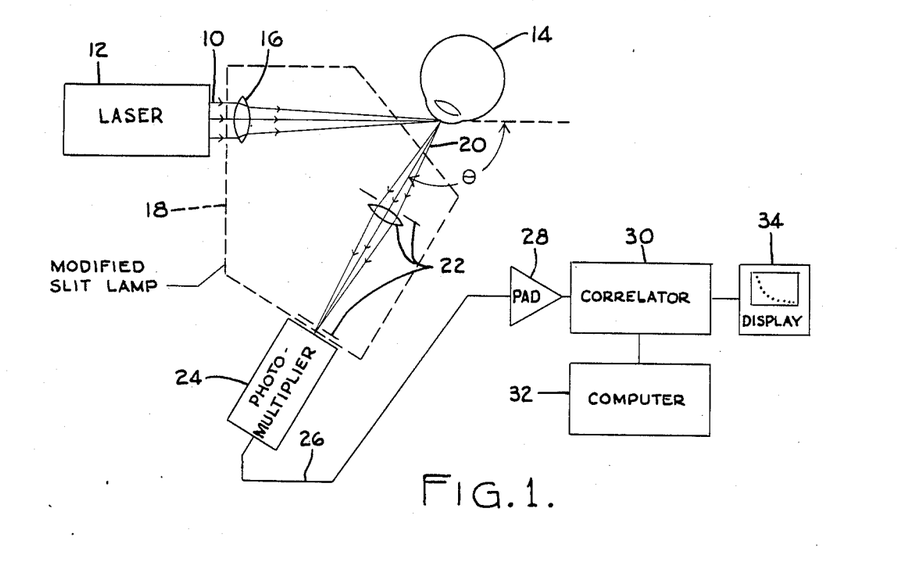
FIG. 1 is a schematic block diagram illustrating the method and apparatus according to the present invention for non-invasive, in vivo inspection of ocular tissue.

Referring now to FIG. 1, there is shown, briefly, the method and apparatus according to the present invention for in vivo, non-invasive inspection of ocular tissue.

Light 10 from a low power but very coherent laser 12 is guided to the eye 14 of a patient through the optics 16 of a modified slit lamp biomicroscope 18. The operator (not shown in FIG. 1) visualizes the scattered laser light 20 and aligns a pick up 22 to a desired measurement location in the ocular tissue. A measurement is made by pressing an actuator button (not shown). The scattered laser light is converted into an electrical signal by a light detector, for example in the form of a photomultiplier 24, and the electrical signal is applied to signal processing means for measuring time dependent fluctuations in the signal and for sorting the signal into components each characterized by an intensity and a fluctuation rate. In particular, the output of photomultiplier 24 is connected by a line 26 to the input of a pulse amplifier and discriminator 28, the output of which is connected to the input of an autocorrelator 30. A computer 32 is operatively connected to autocorrelator 30, and a display 34 also is connected to autocorrelator 30.

As will be described in detail presently, autocorrelator 30 measures time dependent fluctuations of the electrical signal from photomultiplier 24 and calculates the autocorrelation function associated with the fluctuations. A typical autocorrelation function is represented by the curve designated 36 in FIG. 2 which can be visually observed on display 34. Computer 32 converts the autocorrelation function to a two-component exponential decay curve represented by the dotted line curve 38 in FIG. 2 and computes the amplitudes and fluctuation rates of the two components. The amplitudes and fluctuation rates of these two components are utilized by relating them to two species of protein in the ocular tissue, i.e. large and small portions, whereby the degree of laser light scattering by the two protein species provides information as to the condition of the ocular tissue.

Thus, the fluctuating light signal is sorted into components by autocorrelator 30, and each component is associated with a protein group which may be classified by size, mobility and relative amount. In human lens measurements, for example, the intensity associated with small proteins decreases with patient age while the intensity associated with protein aggregates increases with patient age. Tracking these scattering components may allow the determination of a patient's predisposition for cataract.

Thus, the ocular scattering analyzer of the present invention shown in FIG. 1 greatly extends the capability of slit-lamp microscopy by providing a detailed quantitative measurement of light which is scattered by semi-transparent ocular tissue. Not only does the apparatus measure the total amount of scattered light, but it also quantifies its components which are scattered by the various protein constituents in the tissue. The ocular scattering analyzer offers to the research ophthalmologist a sensitive, non-invasive method for in vivo investigations of early changes in macro-molecular structure associated with cataract formation and corneal edema. The detection and quantification of lenticular and corneal tissue changes during the earliest stages of diseases can aid in the prescription and administration of certain drugs as well as aid in the discovery and utilization of new therapeutic agents. Research applications include studies of protein aggregation in the aging lens, X-ray or ultraviolet light induced cataract, early detection of diabetic cataract, biochemical changes with senile cataract, corneal edema with osmotic stress, contact lens induced edema, protein composition of the aqueous, and viso-elastic properties of the vitreous.

Figure 3:
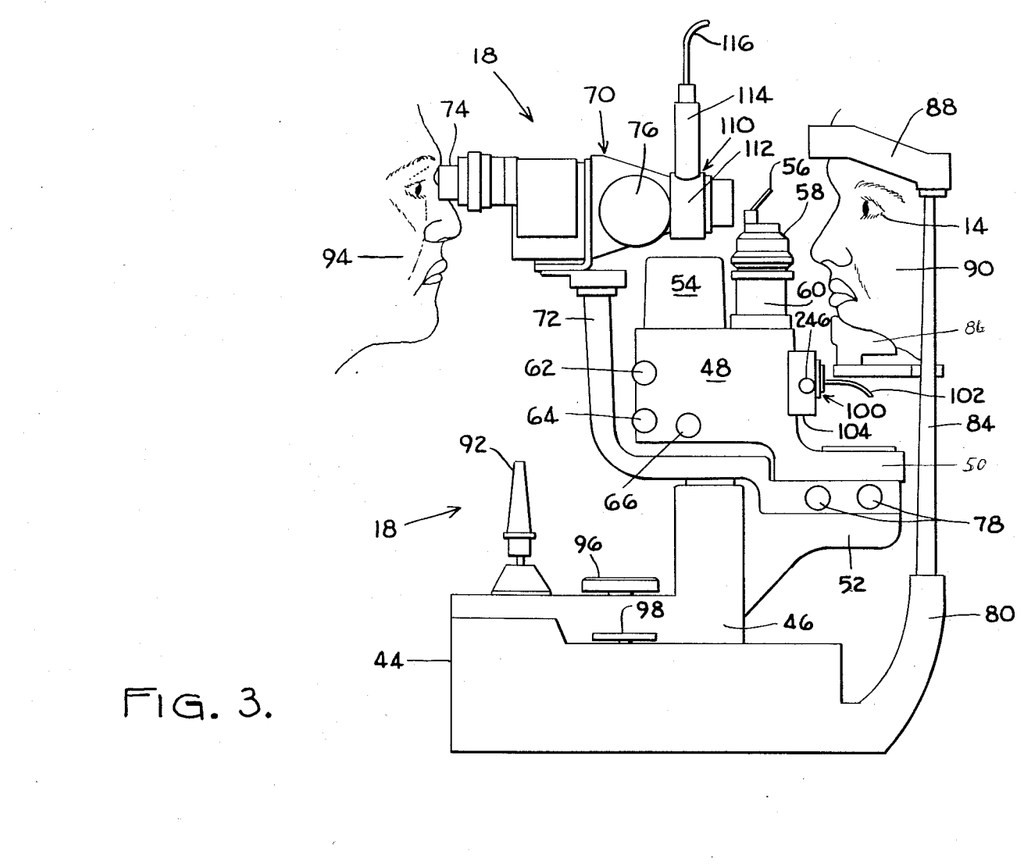
FIG. 3 is a side elevational view, partly diagrammatic, of a modified slit lamp biomicroscope according to the present invention.

FIG. 3 shows in further detail the modified slit lamp biomicroscope 18 according to the present invention. Slit lamp 18 includes a base 44 adapted to rest on a horizontal supporting surface and a vertical post 46 which extends upwardly from base 44. The slit lamp illumination optical system is included within a housing 48 having an offset lower arm 50 pivotally connected to a bracket 52 fixed to post 46. The light source (not shown in FIG. 3) is within a lamp housing 54. A vertical tilt mirror 56 is supported on a collar 58 which, in turn, is mounted on the upper end of a vertical tube 60 extending upwardly from housing 48. The light slit defining system is located within housing 48 below lamp housing 54, and the slit is adjusted by the three knobs designated 62, 64 and 66 for slit length control, slit width control and slit rotation control, respectively. The slit lamp viewing optical system is included within a housing 70 mounted on the upper end of a generally L-shaped arm 72, the lower end of which is pivotally mounted to bracket 52. One end of housing 70 is located near mirror 56, and the opposite end of housing 70 includes a pair of eye pieces, one of which is designated 74. Housing 70 contains a microscope magnification system, adjustment in the magnification being made by a knob 76, the housings 48 and 70 are relatively pivotally movable upon loosening of arm locking knobs 78.

The end of base 44 nearest housing 48 is provided with a pair of upstanding extensions, one of which is designated 80 in FIG. 3, which in turn support a pair of upstanding posts, one of which is designated 84. The posts, in turn, support a lower chin rest 86 and an upper forehead rest 88, both contacted by the head 90 of a patient whose eye 14 is being examined. Movement of the lamp and microscope associated with housings 48 and 70, respectively, is provided by an appropriate mechanism within base 44 in response to manipulation of a joy stick member 92 by the person 94 operating the instrument. This is done to focus the slit image on the patient's cornea or lens, in combination with manipulation of an elevation control knob 96 on base 44 for adjusting the slit image to be level with the patient's eye. The level of illumination provided by the lamp within housing 54 is controlled by a knob 98 on base 44.

In accordance with the present invention, slit lamp 18 is provided with means generally designated 100 for introducing the output light of a laser (not shown in FIG. 3) to the illumination optical system of slit lamp 18 in a manner such that the laser light beam is guided to the patient's eye along the slit of light, i.e. along the same optical path defined by the optics of slit lamp 18 for the slit of light. The laser light is introduced in proximity to the illumination optics of the slit lamp, and this can be done, for example, near or superimposed on the slit or in the section where the beam is collimated, i.e. where the beam is beyond the slit. In the slit lamp shown, means 100 is located on housing 48 on the patient side as shown in FIG. 3 and includes, briefly, a fiber optic cable 102 extending from the output of the laser (not shown in FIG. 3) and terminating in a housing 104 containing an optical system for imaging the laser light from the end of cable 102 in the image plane of the slit of light and in a manner which will be described.

Also in accordance with the present invention, slit lamp 18 is provided with means generally designated 110 operatively associated with the viewing optical system of the slit lamp for receiving scattered laser light from the patient's eye. In the slit lamp shown, receiving means 110 includes a housing comprising a collar portion 112 for adaptation to slit lamp housing 70 and an outwardly extending portion 114 together with a fiber optic cable 116 leading from housing portion 114 to means for converting the scattered laser light into an electrical signal (not shown in FIG. 3). Receiving means also includes means (not shown in FIG. 3) defining a visible target for aligning the laser light visually with said slit of light relative to the patient's eye which will be described in detail presently.

Figure 4:
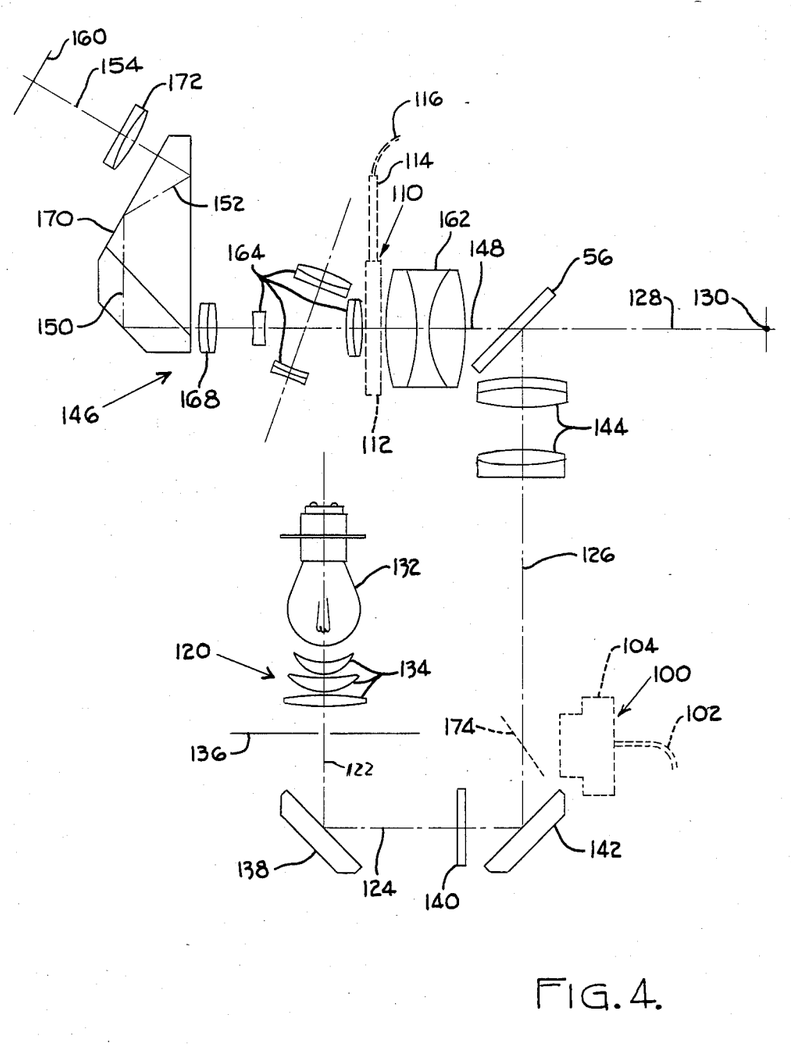
FIG. 4 is a diagrammatic view illustrating the optical system of the apparatus of FIG. 3.

FIG. 4 shows the overall optical system of the slit lamp 18 of FIG. 3. The illumination optical system generally designated 120 forms and images a slit of light along an optical path including portions 122, 124, 126 and 128 to the patient's eye represented by the focal point 130. The illumination system 120 includes a light source in the form of a tungsten filament lamp 132, a condenser lens arrangement 134, an adjustable slit 136, a first mirror 138, a series of light color filters 140, a second mirror 142, an arrangement of focusing lenses 144 and the tilt mirror 56. The viewing optical system generally designated 146 receives, images and magnifies light reflected from the patient's eye illuminated by the slit of light along an optical path including portions 148, 150, 152 and 154 to a focal plane 160 of the viewing system. The viewing optical system includes a focusing lens 162, an adjustable arrangement of magnifying lenses 164, a relay lens 168, a porro prism 170 and a relay lens 172. Focal plane 160 is associated with the eye piece and the eye of the observer (not shown in FIG. 4) and the disposition of optical path 154 corresponds to a slit lamp biomicroscope having inclined viewing eye pieces as compared to horizontal eyepieces as shown in FIG. 3. During a typical measurement, the illumination and viewing optical systems are angularly disposed such that incident and reflected light to and from the patient's eye are at an angle, such as the angle $\theta$ in FIG. 1.

FIG. 4 also shows the relative locations in the optical system of laser light delivery means 100 and scattered laser light receiving means 110. Associated with delivery means 100 is a beam splitter 174 in optical path 126 which will be described in detail presently. By way of example, in an illustrative system, slit lamp biomicroscope 18 is of the type commerically available from Reichert Scientific Instruments, Buffalo, N.Y. under model nos. 11665 or 11666 (inclined or horizontal eyepieces) modified to include delivery means 100 and receiving means 110.

Figure 5:
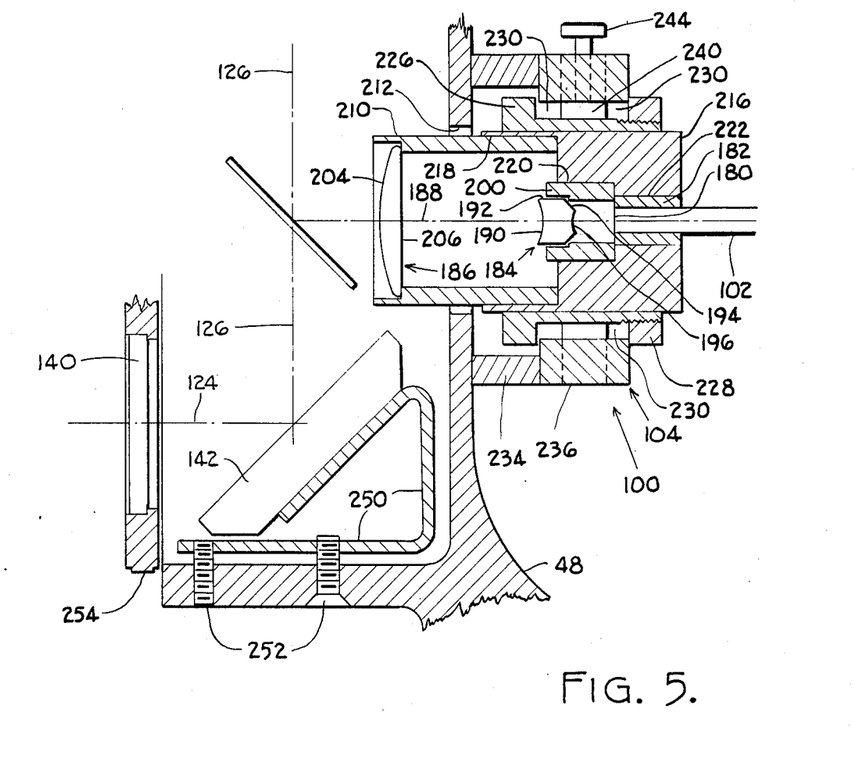
FIG. 5 is a fragmentary sectional view, partly diagrammatic, illustrating the laser light delivery structure in the apparatus of FIGS. 3 and 4.

FIG. 5 shows in detail the laser light delivery means 100 for slit lamp 18 according to the present invention. Fiber optic cable 102 leading from the laser output terminates in an end face 180 within housing 104. The end of fiber optic cable 102 adjacent face 180 is fitted in a sleeve-like holder 182. Between fiber optic end face 180 and beam splitter 174 is an optical system for imaging the laser light in the image plane of the slit of light defined by lamp 18. The optical system includes the combination of a negative power lens 184 and a positive power lens 186 along an optical path 188 extending between optical fiber end face 180 and beam splitter 174. Lens 184 has a concave surface 190 facing lens 186, an annular outer surface 192, a frusto conical surface 194 extending from surface 192 and a concave end surface 196 within surface 194 and facing fiber optic end face 180. Lens 184 is fitted within a sleeve-like holder 200, one end of which abuts holder 182 as shown in FIG. 5. Lens 186 has a convex surface 204 facing beam splitter 174 and a planar surface facing lens 184. Lens 186 is fitted in a sleeve-like holder 210 which, in turn, is located in an opening 212 in the wall of housing 48, opening 212 being slightly larger than the outer diameter of sleeve 210 to permit adjustments in a manner which will be described. Holder 210 is positioned to locate lens 186 within housing 48 near beam splitter 174 and mirror 142 as shown in FIG. 5. The portion of sleeve 210 extending out from housing 48 is received in another sleeve-like holder 216 having a first inner diameter portion 218 receiving holder 210, a second diameter portion 220 receiving sleeve 200 and a third diameter portion receiving bushing 182.

Sleeve 216 thus holds the entire optical assembly. It is located within the combination of a sleeve-like centering cell collar 226 and a centering cell threaded ring 228. Collar 226 has an annular ring-like formation on the end facing housing 48. An annular space 230 is defined between that formation and ring 228. The entire assembly is contained within the combination of a mounting block 234 and a holder block 236. Block 234 is mounted to housing 48 and block 236 is connected to block 234. An annular space also is defined between block 234 and centering cell 226. The assembly is biased in position by spring means in the form of a torsion strap 240 which is fitted at opposite ends in slots provided in holder block 236 adjacent opposite corners thereof which strap 240 extends around along in contact with a portion of the outer surface of centering cell collar 226. Thus, the spring force of strap 240 acts against collar 226, and the exact location of collar 226 in directions parallel to and perpendicular to the plane of the paper as viewed in FIG. 5 is adjusted by a pair of screws spaced apart ninety degrees, one designated 244 in FIG. 5 and the other designated 246 in FIG. 3. The foregoing adjustments of centering cell collar 226, of course, are imparted to the combination of lenses 184, and 186. Holder 216 and the lens combination is adjusted in a longitudinal direction, i.e. along path 188, by a set screw (not shown) extending through holder block 236 and centering cell collar 226 into engagement with holder 216.

Thus, the output light from the laser travels along fiber optic cable 102 to end face 180 and then through the lenses 184,186 to beam splitter 174 whereupon it travels in the same direction as the slit of light along optical path portions 126 and 128 to the eye of the patient. Beam splitter 174 functions to reflect substantially all the laser light received along optical path 188, the direction of reflection being along path 126 toward lens 144 in the arrangement of FIG. 4. Beam splitter 174 also functions to transmit substantially all light received from mirror 142 along path 126. Various arrangements can be employed for mounting beam splitter 174 to position it in the manner shown in FIG. 5. For example, a mounting component could include a disc-shaped body with central light transmitting opening fitted in the vertical tube or turret 60 and provided with a pair of spaced-apart arms depending from diametrically opposed sides of the disc down into housing 48 and fastened to opposite sides of beam splitter 174 which is inclined in the manner shown in FIG. 5. Alternatively, beam splitter 174 could be mounted by suitable means to holder 210 or to the adjacent inner surface of housing 48.

By way of example, in an illustrative apparatus, optical fiber 102 has a diameter of approximately 43 microns, lens 184 is double concave with a minus 8 mm.

focal length (8 mm diameter 4.4 mm thick), and lens 186 is plano convex with a plus 38 mm focal length (20 mm diameter, 3.7 mm thick). The axial distance between the centers of the lenses is about 21.8 mm, and the distance from the center of lens 186 and fiber optic end face 180 is about 9.5 mm. Beam splitter 174 is a red reflective color separation dichronic filter (45° angle of incidence) commercially available from Corion Corporation, Holliston, Mass. and which is about 83% reflective at the laser wavelength of 633 nanometers.

Figure 6:
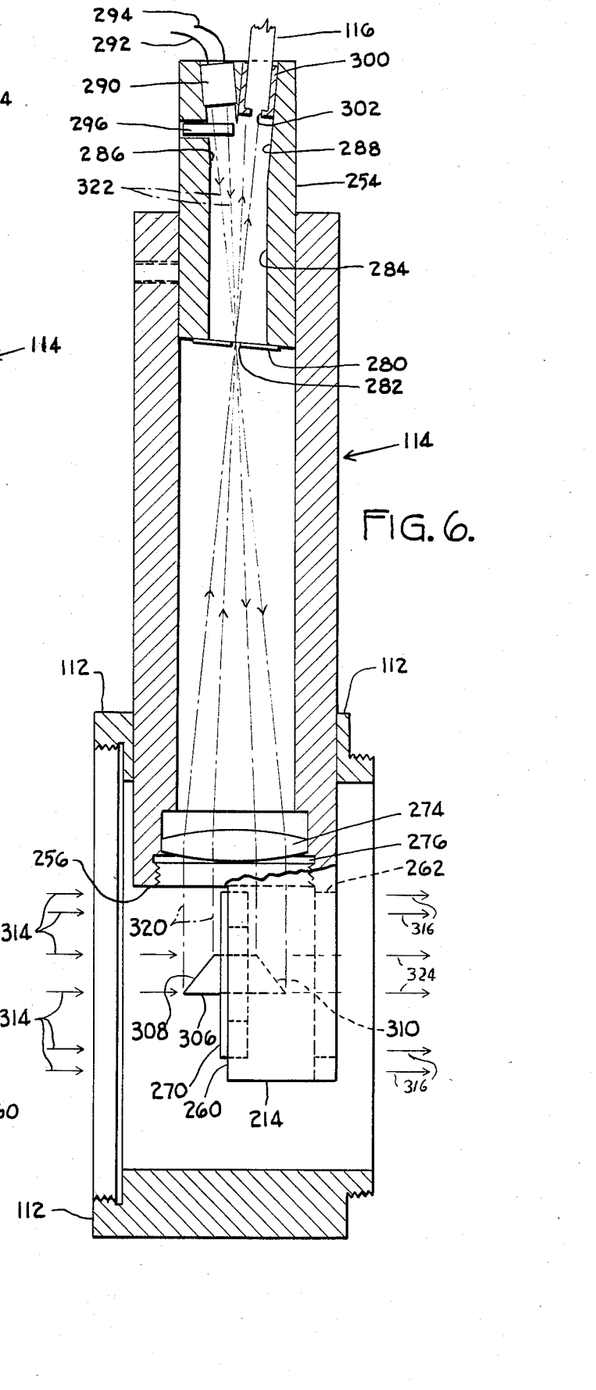
FIG. 6 is a longitudinal sectional view, partly diagrammatic, of the scattered laser light pick up component in the apparatus of FIGS. 3 and 4.
Figure 7:
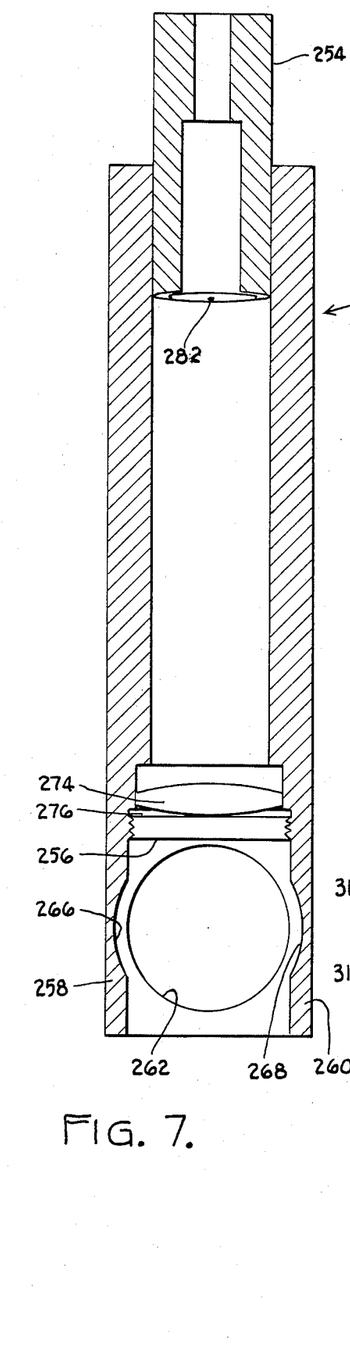
FIG. 7 is a longitudinal sectional view similar to FIG. 6 rotated ninety degrees with parts removed.

FIGS. 6 and 7 show in further detail the means 110 for receiving scattered laser light from the patient's eye. FIG. 6 shows the entire device including collar 112 and extending housing portion 114, and FIG. 7 shows housing portion along with colar 112 and other parts removed. Referring first to FIG. 7, housing portion 114 is in the form of a tube, the outer or upper end of which as viewed in FIG. 7 is fitted with a smaller tube 254 for receiving fiber optic cable 116 and other components as will be described. The opposite or lower end as viewed in FIG. 7 has a section removed extending around one-half the circumference to define an axially disposed edge or surface 256 and longitudinally along the tube wall to define a pair of spaced-apart longitudinal edges 258,260. A circular opening 262 is provided in the wall of tube 114 opposite the opening defined by edges 256,258 and 260 and near the axial end 264 of tube 114. Adjacent edges 258 and 260 a pair of arcuate recesses 266 and 268, respectively, are formed in the inner surface of the tube wall to provide shoulders for receiving a disc 270 of clear glass disposed in a plane parallel to the longitudinal axis of tube 114 and located in alignment with opening 262 as shown in FIG. 6. A collimating lens 274 is located in tube 114 near edge 256 and held by a retaining ring 276 threaded in the tube wall.

The end of tube 254 located within tube 114 is closed by a disc 280 provided with a pinhole or slot 282 generally centrally of tubes 114 and 254 which have a common axis. The interior of tube 254 includes a main passage 284 extending inwardly from disc 280 and a pair of smaller diameter passages 286 and 288 slightly angularly offset and leading from passage 284 to the outer end of tube 254. Passage 286 includes a socket for holding a light emitting diode 290 energized in a suitable manner through leads 292,294, and a color filter 296 located ahead of diode 290. By way of example, in an illustrative device, diode 290 emits green light and filter 296 is selected to pass green light and to reject the red laser light. Passage 288 includes a socket for holding the end of fiber optic cable 116, and within passage 288 is a sleeve-like component 300 defining a round aperture 302 ahead of the end face of cable 116.

The clear glass disc 270 serves as a clear window and is proved with a central opening to receive a mirror element 306 having opposite reflecting faces 308 and 310 at ninety degrees to each other. Mirror element 306 is formed from a single prism having a highly accurate ninety degree angle and shaped to the cylindrical form of element 306. Housing 114 is received in collar 112 which is located in slit lamp housing 70 such that window 270 lies in the beam of parallel light from the patient's eye to the right-hand eyepiece of slit lamp 18.

The receiving means 110 of FIGS. 6 and 7 provides detector and visual monitoring of a specific area of the field of view of the slit lamp microscope. The observer sees the area monitored by the detector as a spot of green light near the center of the field. Light from the patient's eye including reflections from the slit of light illuminating the eye and laser light scattered by the eye tissue enter the region ahead of window 270 as represented by the arrows 314 in FIG. 6. Some of this light travels directly through window 270 as represented by arrows 316 to the eye of the observer. The remainder of this light including scattered laser light is reflected by mirror surface 308 as indicated by the broken lines 320, focused by lens 274 at pinhole 282, which restricts the monitored field of view. It then passes through aperture 302 of the fiber optic socket, which limits the coherence angle, and passes to fiber optic cable 116. Green light from diode 290 follows a reverse path indicated by the broken lines 322 through pinhole 282, is collimated by lens 274, reflected by mirror surface 310 and travels toward the eye of the observer as indicated by arrows 324.

The pinhole 282 defines the monitored field area for both detector and observer. The fields are superimposed when the two beams are parallel. This occurs when the pinhole 282 lies at the focus of lens 274, and the mirror faces 308, 310 are perpendicular to each other, with their normals adjusted to a common plane with the optical axis of lens 274 and pinhole 282. The foregoing spot monitoring capability is provided by a self-contained unit which is not affected by alignment variations of slit lamp 18 as may occur with changes of eyepiece, drum power or pupil separation.

By way of example, in an illustrative device, the longitudinal axes of passage 286 and 288 are disposed each at an angle of about five degrees with respect to the longitudinal axis of tube 114, aperture 302 has a diameter of about 0.012 inch, lens 274 is achromatic and has a focal length of about 48 m and a diameter of about 0.625 inch, and pinhole 282 has a diameter of about 50 microns.

Figure 8:
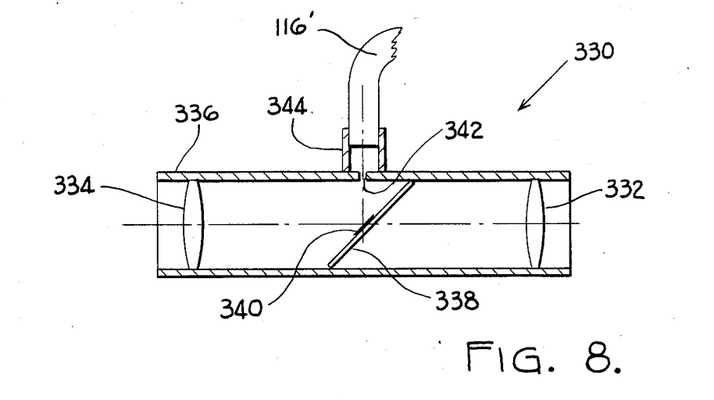
FIG. 8 is a diagrammatic view illustrating an alternative form of pick up.

FIG. 8 shows an alternative focus of pick up device 330 for scattered laser light. Pick up 330 comprises a modified Filar eyepiece which is substituted for one of the eyepieces of slit lamp 18, for example eyepiece 74. For comfort and quality of viewing, a regular Filar eyepiece is substituted for the other eyepiece of slit lamp 18 so that both eyepieces are of substantially the same length. Pickup 330 comprises the combination of an eye lens 332 and a field lens 334 normally found in a Filar eyepiece and which are located in a tubular housing 336. The reticle or scale of a Filar eyepiece is removed and replaced by a beam splitter 338 provided with a small area of reflective coating material 340 on the surface facing lens 334. Housing 336 is modified to include a pinhole 342 aligned with coating 340 and located within a socket 344 into which is fitted the end of a fiber optic cable 116′.

Light from the patient's eye including reflections from the slit of light illuminating the eye and laser light scattered by the eye tissue enters the pickup 330 at the left hand end as viewed in FIG. 8 and is focused by lens 334 toward beam splitter 338 wherein a portion travels further along toward lens 332 which focuses the light to the eye of the observer and another portion is reflected by coating 340 through pinhole 342 to the fiber optic cable 116′.

Figure 9:
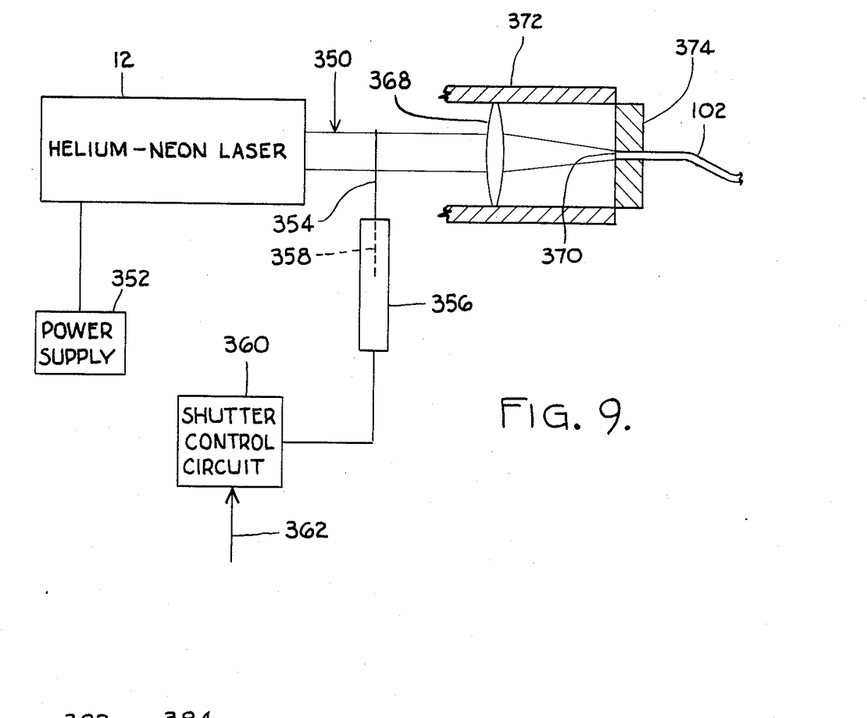
FIG. 9 is a block diagram illustrating the laser, shutter and fiber optic delivery in the apparatus of the present invention.

The arrangement according to the present invention for delivering output light from laser 12 to fiber optic cable 102 for introduction to slit lamp 18 is illustrated in FIG. 9. Laser 12 is a helium-neon laser and provides an output beam 350 of low power, coherent and uniform light. A power supply 352 associated with laser 12 is operated from standard line voltage. There is proved a shutter 354 operatively associated with the output beam 350 of laser 12 and has a first state allowing transmission of a minor fraction of the laser light and a second state allowing transmission of all of the laser light. For example, shutter 354 can comprise an element of gray glass which when interposed entirely in beam 350 as shown in FIG. 9 allows transmission of only about 25 percent of the laser light. There is also provided control means operatively connected to shutter 354 for maintaining the shutter in the first state during adjustments and alignments prior to a measurement and for moving shutter 354 to the second state during a measurement. In the arrangement shown, the control means includes a solenoid generally designated 356 wherein shutter 354 is connected to the solenoid plunger 358. Solenoid 356 is operated by a shutter control circuit 360 in response to an input control signal on line 362. Line 362, in turn, can be operatively connected to a push button switch activated by the operator when a measurement is to take place. Thus, shutter 354 is shown in FIG. 9 in the first state blocking a major portion of beam 350. In response to a control signal on line 362, circuit 360 energizes solenoid 356 for a predetermined measurement time, for example about two seconds, to retract the plunger 358 and move shutter 354 entirely out of the path of beam 350 thereby allowing transmission of the entire output of laser 12.

The laser output beam 350 is focused by a lens 368 onto the end face 370 of fiber optic cable 102. Lens 368 is mounted in a housing 372, and the end of cable 102 adjacent end face 370 in held in a block element 374 adjustably mounted on housing 372 to provide adjustment in X,Y and Z directions in a manner similar to the arrangement of FIG. 5. By way of example, in an illustrative arrangement, laser 12 is a Melles Griot Model 05-LHP-141 helium-neon laser providing laser power to the patient's eye of about 1 milliwatt with shutter 254 open and about 0.05 milliwatt with shutter 354 closed and at a wavelength of about 633 nanometers. Lens 368 is a 4X microscope objective lens. The entire arrangement of FIG. 9 can be contained in the housing of autocorrelator 30, although other locations in the apparatus can be utilized.

Figure 10:
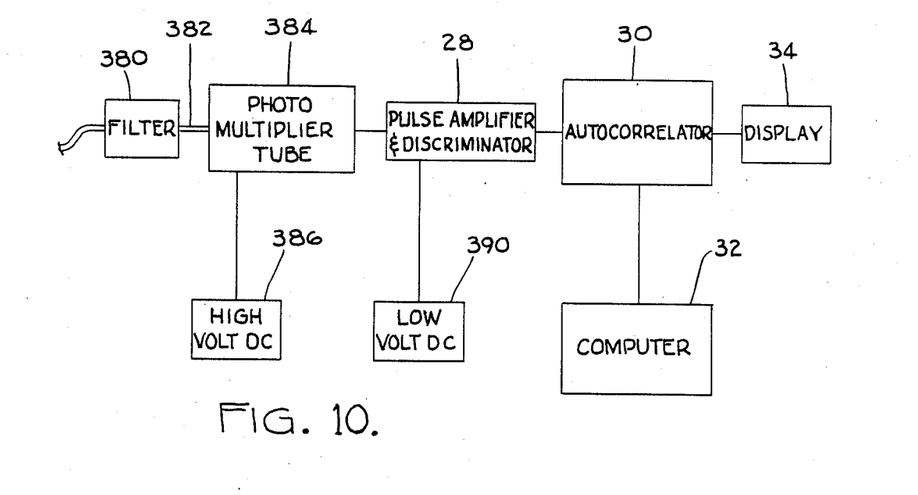
FIG. 10 is a block diagram illustrating the light-to-electrical signal conversion and signal analysis portion of the apparatus of the present invention.

FIG. 10 illustrates the arrangement whereby scattered laser light received by pickup 110 and transmitted by fiber optic cable 116 is converted into electrical signals which are processed by autocorrelator 30. The end of cable 116 is positioned near the input face of an optical band pass filter 380 which passes only the laser light and rejects all other frequencies. The output of filter 380 is positioned near, or alternatively connected by a fiber optic cable 382, to the input of a photomultiplier tube 384 for converting the scattered laser light into an electrical signal. A high voltage d.c. power supply 386 operated from ordinary line voltage is associated with photomultiplier 384. The scattered laser light input to photomultiplier 384 fluctuates in time due to the random motion, i.e. Brownian motion, of the protein molecules in the ocular tissue of the patient. The photomultiplier 384 converts the fluctuating light signal to a corresponding electrical signal comprising a series of pulses. The photomultiplier 384 is used in a photon counting mode wherein the output electrical pulses correspond to photons in the scattered laser light signal. Alternatively, the photomultiplier could be operated in an analog mode. As a further alternative, other light detectors such as solid state light detectors of the silicon type could be employed.

The pulse signal output of photomultiplier 384 is applied to the input of a pulse amplifier and discriminator 28 which functions to remove the very low power pulses which are associated typically with photomultiplier noise. A lower voltage d.c. power supply 390 associated with pulse amplifier and discriminator 28 is operated from ordinary line voltage. The output of pulse amplifier and discriminator 28 is applied to the input of autocorrelator 30 which is operatively associated with computer 32 and display 34. Autocorrelator 30 operates, briefly, in the following manner. Photomultiplier 384 operates as a photon counter to detect fluctuations in the diffraction pattern as protein molecules in the ocular tissue undergo Brownian motion. These intensity changes occur on the order of milliseconds or less, depending upon particle size. Photon correlation spectroscopy provides the means to analyze these intensity fluctuations which are characteristic of particles in solution. The most convenient and accurate analysis of these intensity fluctuations is performed by computing the autocorrelation function of the measured intensities, $G(\tau)$, where $$G(\tau) = \overline{I(t) \times I(t+\tau)}$$

Figure 2:
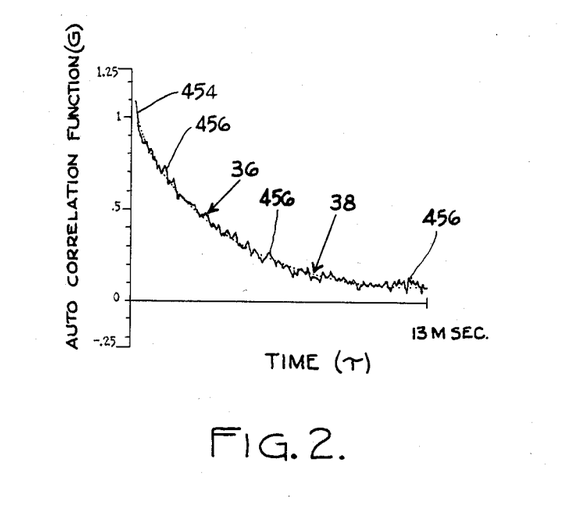
FIG. 2 is a graph of the autocorrelation function during a measurement time obtained by signal analysis in the method and appartus of FIG. 1.

$G(\tau)$ is a time average of the scatter intensity at time t, I(t), times the intensity at a time $\tau$ later, or I(t+$\tau$) where $\tau$ is on the order of milliseconds or microseconds. The autocorrelation function is determined for a number of values of $\tau$ simultaneously, and the data is plotted as $G(\tau)$ versus $\tau$ as shown in FIG. 2. If the molecules or particles in solution are the same size and shape, the curve of the autocorrelation function of the scattered light intensity is a single decaying exponential with a baseline:

$$G(\tau) = a + b \exp(-2\Gamma\tau)$$

The decay rate of the exponential is $2\Gamma \cdot \Gamma$ equals $DK^2$, where D is the diffusion coefficient and $$K = 4\pi n/\lambda \operatorname{Sin}(\theta/2)$$

$$\Gamma = DK^2$$

K represents the following constant parameters: n is the fluid index of refraction, $\lambda$ is the laser wavelength in air, and $\theta$ is the angle at which the scattering intensity is measured as shown in FIG. 1. The diffusion coefficient D is inversely related to the particle size according to the Stokes - Einstein equation:

$$D = KT/3\pi\eta d$$

where K is the Boltzmann constant, d is the diameter of the particle and $\eta$ is the viscosity of the solution at a constant temperature T.

Autocorrelator 30 looks for variations in constancy of a signal and the frequency and amplitude content of those variations including the average time between pulses. In particular, autocorrelator 30 calculates $G(\tau)$ for 64 values of $\tau$ and displays the data as an autocorrelation function histogram on a video screen, i.e. on display 34. The average of the delayed last eight channels of the autocorrelation function determines the baseline of $G(\tau)$. Using a curve fitting algorithm in a known manner with computer 32 enables $\Gamma$ to be found which permits information to be obtained about average particle size and viscosity when other parameters such as $\lambda$, n,θ and T are used in the calculations. If the molecules or particles in solution have a range of sizes and shapes, the autocorrelation function is comprised of a weighted sum of exponentials where each term represents a particular size/shape range. Using a curve fitting routine in a known manner with computer 32 for the exponential-type autocorrelation function, a polydispersity factor ($\mu^2/\Gamma^2$) is calculated. This factor is the ratio of the variance of the decay rate distribution to the square of the average decay rate.

By way of example, in an illustrative apparatus photomulitplier 384 is a Thorn EMI Gencom model 9863/350B, autocorrelator 30 is a Brookhaven Instruments Model 2030 digitial correlator with 72 real-time data channels capable of measuring up to 4 sample times simultaneously in the 100 nanosecond to 990 millisecond range, and computer 32 is an IBM personal computer, model XT with 128 kilobyte memory, 360 kilobyte diskette drive and 10 megabyte hard disc storage. A frequency analyzer can be employed as an alternative to the autocorrelator.

The ocular scattering analyzer of the present invention operates in the following manner. Before making a measurement, the operator 46 selects from a keyboard (not shown) associated with autocorrelator 30 the desired instrument settings which include the time duration of the measurement, the proper time scale for the measurement and the sensitivity of the instrument to light. The operator also can enter into computer 32 medical information about patient 90 and the location in the patient's eye 14 where the measurement will be taken. Then the operator 46 positions modified slit lamp 18 relative to the patient 90 as shown in FIG. 3 and operates the controls including joy stick 92 and elevation control 96 to move the slit of light to illuminate the desired location in the patient's eye. Simultaneously, with shutter 354 in the position of FIG. 9 the lower level of laser light is focused to the patient's eye in the same direction of the slit of light. The mechanisms and optics of modified slit lamp 18 advantageously allows the operator 46 to position the focused laser beam anywhere in the anterior section of the patient's eye 14. A further advantage is that simultaneously the operator 46 can view the region illuminated by the laser.

Figure 11:
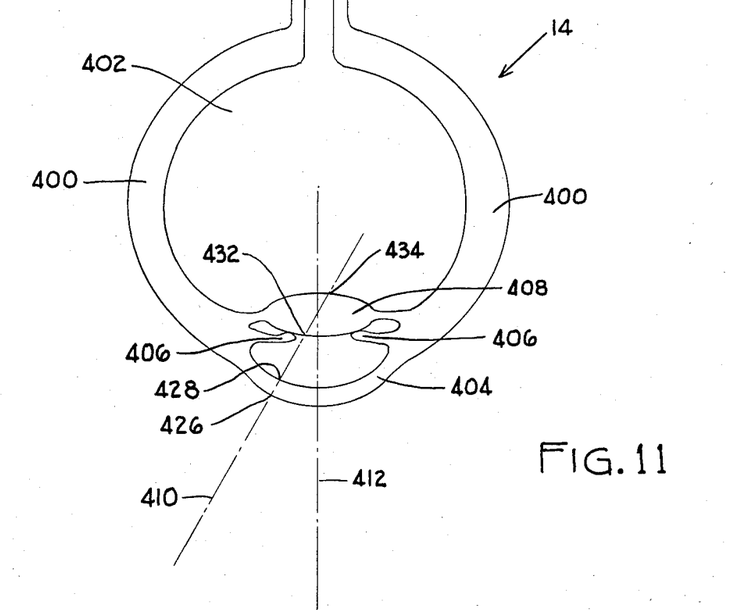
FIG. 11 is a schematic diagram illustrating one aspect of the method of the present invention.
Figure 12:
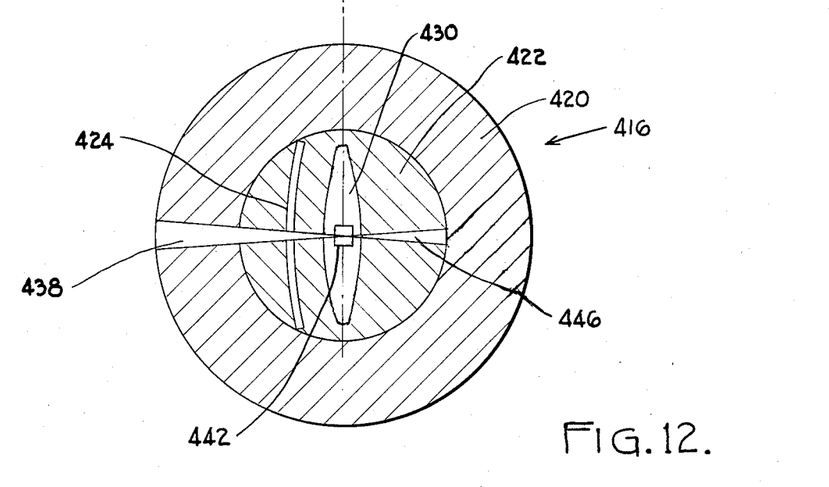
FIG. 12 is a schematic diagram illustrating another aspect of the method of the present invention.

The foregoing is illustrated further by FIG. 11 which shows application of light to the patient's eye and FIG. 12 which shows the image seen by the operator. Referring first to FIG. 11, the patient's eye includes exterior tissue 400, interior vitreous 402, corena 404, iris 406 and lens 408. The slit illumination axis is designated 410, i.e. it is the direction traveled by the slit of light from slit lamp biomicroscope 18 into the patient's eye 14. The focused beam of laser light also travels in this direction. The observer viewing axis is designated 412, i.e. it is the direction of viewing by operator 46 looking through slit lamp biomicroscope 18 toward the patient's eye 14. The image seen by operator 46 looking along axis 412 is illustrated in FIG. 12. The image 416 includes an outer ring-like section 420 corresponding to the patient's irisand an inner disc-like section 422 corresponding to the patient's pupil. The corneal image of slit lamp illumination is represented by the region 424 in FIG. 12, This corresponds to the region between points 426 and 428 in FIG. 11. The lens image of slit lamp illumination is represented by the region 430 in FIG. 12. It corresponds to the region between points 432 and 434 in FIG. 11. The incoming focused beam of laser light is indicated as 438, the target is represented at 442 and the remainder of the laser beam is indicated as 446. Target 442, formed by the image of the green light from light emitting diode 290 in pick up 110 can be rectangular in shape as shown in FIG. 12 or it can be circular or any other shape depending upon the shape of pinhole 282 in pick up 110. Thus, as operator 46 manipulates the joy stick 92 and elevation control 96 to move the slit of light and laser beam relative to the patient's eye, target 442 likewise moves. Thus, target 442 serves as a guide to line up the exact location on the ocular tissue where laser light is to be applied for scattering back to the instrument and ultimate analysis.

Thus, after the instrument settings are made and patient input data provided, the operator 46 positions the pickup, i.e. target 442, at the desired location in the ocular tissue and initiates a measurement by pushing a button. This applied a signal to line 362 in the arrangement of FIG. 9 causing control circuit 360 to operate solenoid 356 to open shutter 354, allowing the optical beam delivery system to direct a low-power laser beam into the ocular tissue of the patient. Simultaneously, the signal applied to line 362 is utilized to place autocorrelator 30 in an operating mode to process the scattered light signal. A measurement typically lasts for two seconds after which time shutter 354 closes and autocorrelator 30 is switched out of the operating mode. During the measurement, the scattered light enters the receiver optics 110 and is directed to photomultiplier 384. Because the scattering proteins move about randomly inside the ocular tissue, the scattered light also fluctuates in time. Photomultiplier 384 converts the fluctuating light signal to a corresponding electrical signal that is processed and displayed by autocorrelator 30.

The operation of autocorrelator 30, previously described, may be summarized as follows. It is used to analyze the fluctuations in the intensity of laser light scattered by the ocular tissue. The random motions of crystalline proteins give rise to concentration flucutuations, and the intensity of scattered light fluctuates accordingly. The scattered light is recorded in the form of a time correlation function, which relates the scattered light intensity at a time t, I(t) to that at a certain time $\tau$ later $I(t+\tau): <I(t)I(t+\tau)>$ where $< >$ denotes averaging over the entire measurement duration. Briefly, the correlation function decays exponentially with characteristic decay times which directly relate to the diffusivity of the protein groups.

The principles of measurement are as follows. The motion of macromolecules caused by thermal agitation and the random striking of neighboring molecules in solution is called Brownian motion. The effect of the random impacts on the suspended macromolecules causes time to vibrate and diffuse randomly about their local environment. In the lens of the human eye, the constantly changing distribution of protein molecules while in Brownian motion can be analyzed by quasi-elastic light scattering. The ocular scattering analyzer of the present invention measures the time dependent fluctuations of laser light scattered by protein macromolecules, and calculates the autocorrelation function, $G(\tau)$, associated with these fluctuations. From the autocorrelation function the computer 32 calculates the amplitudes and characteristic fluctuation rates of protein species. In the human lens, measurements obtained using the method of the present invention indicate that there are two dominant classes of protein. One is small, rapidly moving proteins which contribute to the rapidly decaying portion 454 of the exponential curve in FIG.

2. The other is large, slowly moving proteins which contribute to the more gradually decaying portion 456 of the exponential curve in FIG. 2.

If the molecules or particles in solution have the same size and shape (monodispersity), the curve of the autocorrelation function of the scattered light intensity is a single decaying exponential with a baseline:

$$G(\tau) = a + b \exp(-2\Gamma\tau)$$

The decay rate of the exponential is $2\Gamma \cdot \Gamma$ is related to the difussion coefficient D, as shown below.

$$\Gamma = DK^2 \text{ where}$$

$$K = 4\pi\eta/\lambda \sin(\theta/2)$$

In the second equation, n is the fluid index of refraction, $\lambda$ is the laser wavelength in air, and $\theta$ is the angle at which the scattered intensity is measured.

In the case of the human lens, as previously explained the autocorrelation function has the form of a two-component exponential.

$$G(\tau) = a + [I_1 \exp(-\Gamma_1\tau) + I_2 \exp(-\Gamma_2\tau)]^2$$

where $I_1$ represents the amplitude of light scattered by the large proteins, $I_2$ the amplitude of light scattered by the small proteins $\Gamma_1$ is the fluctuation rate of light scattered by the large proteins and $\Gamma_2$ is the fluctuation rate of light scattered by the small protein.

Thus, from a measurement taken on a patient the autocorrelation function 36 in FIG. 2 is obtained via autocorrelator 30. As indicated in FIG. 2 the magnitude of $\tau$ for such measurement typically is 13 milliseconds. Computer 32 converts the autocorrelation function to a two component exponential decay curve 38 using known curve fitting techniques, and computes the amplitudes $I_1$ and $I_2$ and fluctuation rates $\Gamma_1$ and $\Gamma_2$ for the patient.

Figure 13:
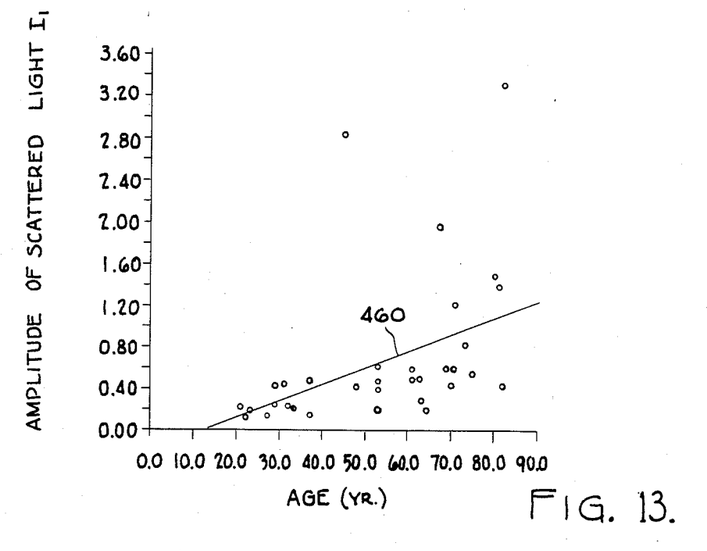
FIG. 13 is a graph showing amplitude of light scattered by large aggregated proteins as a function of age of a human subject prepared from information developed by the method and apparatus of the present invention.
Figure 14:
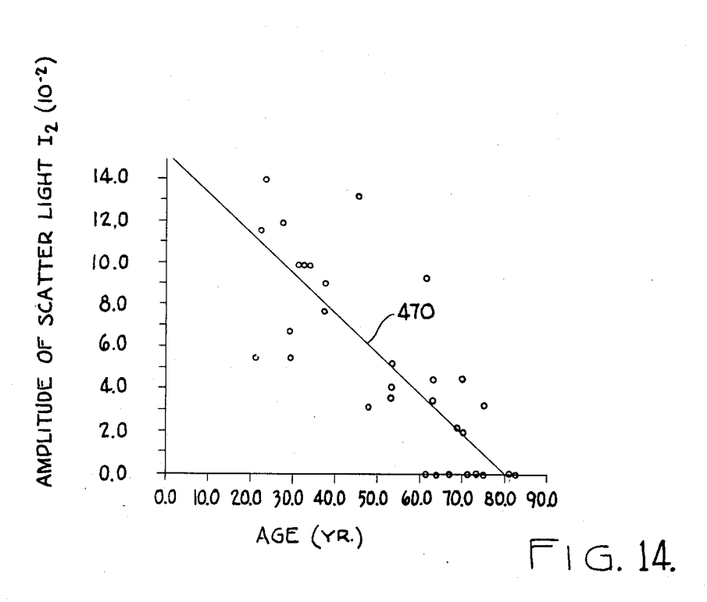
FIG. 14 is a graph showing amplitude of light scattered by small proteins as a function of age of a human subject prepared from information developed by the method and apparatus of the present invention.

Using the values of $I_1$ and $I_2$ obtained from a number of patients, the behavior of these quantities as a function of age can be determined. In particular, FIG. 13 is a graph of amplitude of light scattered by large aggregated proteins, $I_1$, as a function of age of human subject. Each point represents a measurement taken on a single individual. The measurement location was at the anterior section of the nucleus along the optic axis of the lens. Line 460 is a linear regression representing the best fit of the data. FIG. 14 is a graph of amplitude of light scattered by small proteins, $I_2$, as a function of age of the human subject. Each point represents a measurement taken on a single individual. The measurement location was at the anterior section of the nucleus along the optic axis of the lens. Line 470 is a linear regression representing the best fit of the data.

Data of the type presented in FIGS. 13 and 14 can be used in analysis of lens condition of subsequent patients. Values of $I_1$ and $I_2$ for a patient are obtained using the ocular scattering analyzer of the present invention. The $I_1$ and $I_2$ values for a patient are compared to the data of FIGS. 13 and 14 and the closer the patients $I_1$ and $I_2$ values are to lines 460 and 470, respectively, in FIGS. 13 and 14 the closer that patient's lens is determined to be normal. The $I_1$ and $I_2$ values for a number of patients can be stored in computer 32 to form a data base, typically for a normal group, and computer 32 subsequently can make a comparison between those stored values and the values fro a particular patient.

Investigating the temporal fluctuations of scattered laser light, Tanaka and Benedek measured the diffusivity of proteins within the human lens and observed significantly lower diffusivities with cataractous human lenses, which indicatedprotein aggregation with cataractogenesis. Tanaka T, Benedek GB: *Invest Ophthalmol* 1975; 14: 449. They concluded that the aggregated proteins were about five times larger in diameter than those in the normal lens and had molecular weights of about $5 \times 10^8$ daltons. Their results compared fairly well to molecular weight determinations of protein aggregates done with gel filtration. It is thought that the aggregates are formed from lower molecular weight protein constituents of the lens.

Results obtained using the method of the present invention show the increase with human age of light scattering from the large aggregated proteins (FIG. 13), and the corresponding decrease with human age of light scattering from the lower molecular weight crystallins (FIG. 14). The subjects for the study included both normal individuals and patients with some degree of cataract formation.

In the operation of computer 32 with respect to autocorrelator 30 previously described, computer 32 can be used to analyze a measurement, i.e. curve 36 in FIG. 2. The computer reads the measurement and plots the derived data set. The next phase in the operation of computer 32 is fitting the data, i.e. to an exponential decay curve similar to curve 38 in FIG. 2. As an alternative to the two component approach described herein, there can be obtained a set of experimental points fitted by a curve resulting from a cumulants analysis of the experimental points.

It is therefore apparent that the present invention accomplishes its intended objects. While an embodiment of the present invention has been described in detail, that is for the purpose of illustration, not limitation.

I claim:

1. Apparatus for in vivo inspection of ocular tissue comprising:
   (a) a slit lamp biomicroscope including an illumination optical system comprising a light source, means defining a slit of light and means for imaging the slit of light into the eye of a patient and including a viewing optical system observing light reflected from the eye illuminated by said slit of light;
   (b) a laser for providing a low power, coherent and uniform output beam of light;
   (c) means for introducing said laser output light beam to said illumination optical system of said slit lamp in a manner such that said laser light beam is guided to the patient's eye in a direction of said slit of light;
   (d) means operatively associated with said viewing optical system of said slit lamp for receiving scattered laser light from the patient's eye;
   (e) means for converting the scattered laser light into an electrical signal; and
   (f) signal processing means for measuring time dependent fluctuations in said signal and sorting said signal into components each characterized by an intensity and a fluctuation rate.

2. Apparatus according to claim 1, further including display means operatively connected to said signal processing means for providing a visual display of processed signals.

3. Apparatus according to claim 1, wherein said signal processing means comprises:

(a) autocorrelator means for measuring time dependent fluctuations of said signal and calculating the autocorrelation function associated with said fluctuations; and
(b) computer means operatively connected to said autocorrelator means for converting said autocorrelation function to a two-component exponential decay curve and computing the amplitudes and fluctuation rates of said two components;

4. Apparatus according to claim 1, wherein said receiving means includes means defining a visible target for aligning the laser light visually with said slit of light relative to a particular measurement site in the patient's eye.

5. Apparatus according to claim 1, wherein said converting means includes means for transforming scattered laser light into pulse signals having a frequency influenced by the nature of the scattering.

6. Apparatus according to claim 1, wherein said signal converting means comprises a photomultiplier.

7. Apparatus according to claim 1 further including
(a) a shutter operatively associated with the output of said laser and having a first state allowing transmission of a minor fraction of said laser light and a second state allowing transmission of all of said laser light;
(b) control means operatively connected to said shutter for maintaining said shutter in said first state during adjustments and alignments prior to a measurement and for moving said shutter to said second state during a measurement.

8. Apparatus according to claim 1, wherein said laser is located remote from said slit lamp and further including fiber optic means for transmitting said laser output to said illumination optical system of said slit lamp.

9. Apparatus according to claim 1, wherein said means for introducing said laser output light to said slit lamp includes optical means for imagining the laser light in the image plane of the slit of light.

10. Apparatus according to claim 9, further including linear adjustment means operatively associated with said optical means.

11. A method for non-invasive in vivo inspection of ocular tissue comprising the steps of:
(a) guiding low power, uniform and coherent laser light through the optical system of a slit lamp biomicroscope to the eye of a patient for scattering by protein molecules in the ocular tissue of the patient;
(b) viewing scattered laser light in the ocular tissue through the slit lamp to visually align a pick up associated with the slit lamp optical system to a desired measurement location in the ocular tissue;
(c) performing a measurement by receiving laser light scattered from the ocular tissue and converting the scattered light into an electrical signal; and
(d) analyzing the electrical signal by obtaining at least one component characterized by an intensity and a fluctuation rate which component is associated with a protein group in the ocular tissue.

12. A method according to claim 11, wherein said step of analyzing the electrical signal comprises sorting the signal into components each characterized by an intensity and a fluctuation rate and each component associated with a protein group in the ocular tissue.

13. A method according to claim 11 wherein said step of analyzing the electrical signal comprises the steps of:
(a) measuring time dependent fluctuations of said signal and calculating the autocorrelation function associated with said fluctuations;
(b) converting said autocorrelation function to an exponential decay curve;
(c) computing the amplitude and fluctuation rate associated with said curve; and
(d) utilizing said amplitude and fluctuation rate of said curve by relating them to protein in said ocular tissue whereby the relative degree of laser light scattering by said protein provides information as to the condition of the ocular tissue.

14. A method according to claim 11 wherein said step of analyzing the electrical signal comprises the steps of:
(a) measuring time dependent fluctuations of said signal and calculating the autocorrelation function associated with said fluctuations;
(b) converting said autocorrelation function to a two-component exponential decay curve;
(c) computing the amplitudes and fluctuation rates of said two components; and
(d) utilizing said amplitudes and fluctuation rates of said two components by relating them to two species of protein in said ocular tissue whereby the relative degree of laser light scattering by said two protein species provides information as to the condition of the ocular tissue.

15. A method according to claim 11 further including controlling the level of said laser light between a low level during said step of viewing and a high level during said step of performing a measurement.

16. A method according to claim 11 further including the step of displaying the analyzed signal.

17. A method according to claim 13 further including the step of displaying said autocorrelation function.

18. A method for non-invasive in vivo inspection of ocular tissue comprising the steps of:
(a) directing low power, uniform, coherent laser light to the eye of a patient for scattering by protein molecules in the ocular tissue of the patient;
(b) receiving laser light scattered from the ocular tissue and converting the scattered light into an electrical signal;
(c) measuring time dependent fluctuations of said signal and calculating the autocorrelation function associated with said fluctuations;
(d) converting said autocorrelation function to a two-component exponential decay curve;
(e) computing the amplitudes and fluctuation rates of said two components; and
(f) utilizing said amplitudes and fluctuation rates of said two components by relating them to two species of protein in said ocular tissue whereby the relative degree of laser light scattering by said two protein species provides information as to the condition of the ocular tissue.

19. A method according to claim 18 further including:
(a) storing said amplitude and fluctuation rates for a number of measurements conducted on a plurality of patients to form a data base; and
(b) comparing the amplitude and fluctuation rate obtained from a measurement on a particular patient to the amplitude and fluctuation rates of said data base.

20. A method according to claim 14 further including:
(a) storing said amplitude and fluctuation rates for a number of measurements conducted on a plurality of patients to form a data base; and
(b) comparing the amplitude and fluctuation rate obtained from a measurement on a particular patient to the amplitude and fluctuation rates of said data base.

* * * * *